United States Patent
Haruna et al.

(10) Patent No.: US 9,399,147 B2
(45) Date of Patent: Jul. 26, 2016

(54) PARTICLE BEAM IRRADIATION CHAMBER

(71) Applicant: Mitsubishi Electric Corporation, Chiyoda-ku, Tokyo (JP)

(72) Inventors: Nobuyuki Haruna, Tokyo (JP); Yusuke Sakamoto, Tokyo (JP); Tadashi Katayose, Tokyo (JP)

(73) Assignee: MITSUBISHI ELECTRIC CORPORATION, Chiyoda-Ku, Tokyo (JP)

(*) Notice: Subject to any disclaimer, the term of this patent is extended or adjusted under 35 U.S.C. 154(b) by 0 days.

(21) Appl. No.: 14/772,696

(22) PCT Filed: Mar. 20, 2014

(86) PCT No.: PCT/JP2014/057763
§ 371 (c)(1),
(2) Date: Sep. 3, 2015

(87) PCT Pub. No.: WO2014/167973
PCT Pub. Date: Oct. 16, 2014

(65) Prior Publication Data
US 2016/0016011 A1  Jan. 21, 2016

(30) Foreign Application Priority Data
Apr. 10, 2013 (JP) .................. 2013-082310

(51) Int. Cl.
*A61N 5/10* (2006.01)
*G21F 7/005* (2006.01)

(52) U.S. Cl.
CPC ............... *A61N 5/1081* (2013.01); *A61N 5/10* (2013.01); *G21F 7/005* (2013.01); *A61N 5/1077* (2013.01); *A61N 2005/1087* (2013.01); *A61N 2005/1094* (2013.01)

(58) Field of Classification Search
CPC ...... A61N 5/1081; A61N 5/1077; A61N 5/10
See application file for complete search history.

(56) References Cited

U.S. PATENT DOCUMENTS 8,384,054 B2 * 2/2013 Fehrenbacher ............ 250/505.1
2010/0171045 A1   7/2010 Güneysel
(Continued)

FOREIGN PATENT DOCUMENTS

EP        0 888 622 B1    6/2002
EP        2 535 086 A1   12/2012
(Continued)

OTHER PUBLICATIONS

International Search Report (PCT/ISA/210) mailed on Apr. 28, 2014, by the Japanese Patent Office as the International Searching Authority for International Application No. PCT/JP2014/057763.
(Continued)

*Primary Examiner* — Wyatt Stoffa
*Assistant Examiner* — Sean Luck
(74) *Attorney, Agent, or Firm* — Buchanan Ingersoll & Rooney PC (57) ABSTRACT

A particle beam irradiation chamber in which a passage having a first opening part at a side of an inner wall and a second opening part at a side of an outer wall is provided and which has an isocenter inside the chamber, wherein a first line segment which connects the center of the first opening part and the center of the second opening part passes inside the passage, an angle, which is formed by a second segment, which connects the center of the first opening part and the isocenter and the first line segment, is smaller than 180 degrees, and a width of the passage is narrower than a width of opening of the first opening part.

7 Claims, 7 Drawing Sheets

(56) References Cited

U.S. PATENT DOCUMENTS

| | | |
|---|---|---|
| 2012/0159849 A1 | 6/2012 | Farrell |
| 2013/0066134 A1* | 3/2013 | Carol ................... A61N 5/1079 600/1 |
| 2013/0317343 A1 | 11/2013 | Klimenko et al. |

FOREIGN PATENT DOCUMENTS

| | | |
|---|---|---|
| JP | 43-6515 B1 | 3/1968 |
| JP | 05-223987 A | 9/1993 |
| JP | 09-243794 A | 9/1997 |
| JP | 2012-050843 A | 3/2012 |
| JP | 2013-000596 A | 1/2013 |

OTHER PUBLICATIONS

Office Action (Examination Report) issued on Oct. 21, 2015, by the Intellectual Property Office in corresponding Taiwanese Patent Application No. 103112970 and an English translation thereof. (7 pgs).

* cited by examiner

PARTICLE BEAM IRRADIATION CHAMBER

TECHNICAL FIELD

This invention relates to a particle beam irradiation chamber in which a particle beam irradiation device which aims to irradiate a charged particle beam which is accelerated by an accelerator to a target is provided.

BACKGROUND ART

A charged particle beam is circulated and accelerated by an accelerator (circular accelerator) such as a synchrotron, the charged particle beam which is accelerated to be high-energy (mainly, a proton or a carbon ion) is extracted from the circulating orbit, the charged particle beam which becomes a beam-state (will be also referred to as a charged particle beam, or a particle beam) is utilized in a physics experiment or a particle beam therapy such as a cancer treatment in which the charged particle beam is transported by a beam transport system so as to irradiate to an intended object. In a particle beam therapy by an accelerated charged particle beam (hereinafter, will be referred to as a particle beam), a particle beam is transported to an irradiation device which is provided in a particle beam irradiation chamber.

In an irradiation device, a thin beam-like particle beam is scanned and spread by, for example, two sets of deflection electromagnet in directions of two axis which are perpendicular to a beam travelling direction, then, is passed through a scatterer to be spread further, is finally cut out to be a shape of a cancer by a collimator so as to irradiate to a person to be treated. A depth direction irradiation of a particle beam is adjusted to be a depth direction width of a cancer part of a person to be treated by passing the particle beam through a splinter-like filter, for example, so called a ridge filter and spreading a width of energy. The above-mentioned irradiation method of a particle beam is called as a spreading irradiation method. Further, recently, a scanning irradiation method, in which a particle beam whose state is kept thine beam state is scanned only by two sets of deflection electromagnets for beam scanning and is irradiated to a cancer part, is performed.

In a case of a spreading irradiation method, when a particle beam which is accelerated to be high-energy collides with a scatterer or a collimator, finally a body of a person to be treated, radiation such as a neutron beam or a photon beam is generated secondarily. A spot where particle beams which are accelerated to be high-energy are collided and a neutron beam or a photon beam is generated secondarily is called a source of radiation. At this time, a neutron beam which is generated secondarily has energy distribution to the vicinity of energy of incident charged particle beam at most (in a case of particle beam treatment, per nucleon, several hundred MeV). Also, in a case of a scanning irradiation method, frequency of collision with a particle beam and a collimator or a scatterer is low, however, a particle beam is finally irradiated to inside of a body of a person to be treated. Therefore, total amount of a neutron or a photon beam which is generated secondarily is small in comparison with that of a spreading irradiation method, however, high-energy neutron beam or a photon beam is generated.

In a facility where radiation such as a neutron beam or a photon beam is generated, dose limit is specified by laws and regulations. In a particle beam therapy facility, in order to make effective dose of outside a particle beam irradiation chamber to be in a legally permissible range, the intensity of a neutron is attenuated by thickening a thickness of a concrete wall or making a passage from a treatment bed where a person to be treated (patient) is placed in a particle beam irradiation chamber to a door of an entrance of an irradiation chamber to be a labyrinth-like shape (for example, refer to Patent Document 1).

When a particle beam irradiation chamber is designed in shielding manner, two kinds of shielding effects, that is, an effect of bulk shielding and streaming should be considered. Bulk shielding is an effect to attenuate the dose equivalent of a neutron beam or a photon beam which is reached from a source of radiation passing through a concrete wall. In general, when a wall is thick and density of wall material is high, a shielding effect is high. Streaming is an effect of leaking a neutron beam or a photon beam, which is passed through a passage which connects inside and outside of a particle beam irradiation chamber, to the outside chamber. In general, when a passage is longer, cross section of a passage is smaller, and the time of bending is larger, dose equivalent of a neutron beam or a photon beam which leaks outside chamber is reduced by streaming is smaller.

In a case where a shielding design in which a passage is utilized is performed, dose in the vicinity of an entrance of a passage which is a side of a radiation source is maximum dose, and after that dose is attenuated by a distance. Therefore, it is preferable such that dose at the radiation source entrance side of the passage is made to be small as possible. In general, energy of a neutron which is reached without being shielded on the way from a radiation source is not attenuated, therefore contribution to equivalent dose is large. (In strictly speaking, the degree of contribution to dose is different depending on energy, however, in a case of a neutron which is generated in a particle beam therapy, several hundred MeV neutron is generated at most, and contribution to a neutron in a range of several MeV to several hundred MeV is large). Consequently, it is important to attenuate an irradiation dose which intrudes in a passage by reducing the speed of a particle beam with a shielding wall and scattering. Conventionally, not only by making a passage to be a labyrinth-like form but also by forming a convex wall in a labyrinth-like passage, a neutron beam, which is reached from a radiation source to a gateway outside a particle beam irradiation chamber, is attenuated (for example, refer to Patent Document 2).

PRIOR ART REFERENCE

Patent Document

Patent Document 1: JP2012-50843A (P12, FIG. 1)
Patent Document 2: JP-H05-223987A (P6, FIG. 1, FIG. 2, FIG. 3)

DISCLOSURE OF THE INVENTION

Problems to be Solved by the Invention

However, according to conventional shielding design, a passage which is surrounded by a shielding wall is formed to be a labyrinth-like passage, therefore, there is a problem such that an occupation area is large. For example, in a charged particle beam therapy or a photon beam therapy, an amount of radiation which is generated and energy is changed depending on a kind of a particle to be used for a therapy and energy. Consequently, in a case where an area of a particle beam irradiation chamber is compared, it is necessary to compare by considering a particle to be used for a therapy and energy. In comparison with a photon beam therapy, in a particle beam therapy, a neutron having higher energy is generated. Consequently, in order to attenuate radiation, it is necessary to form a thicker shielding wall and a longer passage. Further, a passage which is surrounded by a shielding wall is formed to be a labyrinth-like passage, therefore, a traffic line of a patient who moves from an entrance of a particle beam irradiation chamber to a treatment bed or a traffic line of medical personnel is complicated. Consequently, it takes longer time before starting treatment or it takes longer time for a patient to leave the chamber after treatment. As a result, there is a problem such that throughput of treatment is low.

In order to solve the above-mentioned problem, this invention aims to improve throughput of treatment by making an occupation area smaller and shortening a traffic line of a patient and medical personnel.

Means for Solving the Problems

In a particle beam irradiation chamber of this invention, it is configured such that a passage having a first opening part at the side of an inner wall and a second opening part at the side of an outer wall is provided, an isocenter is provided inside the particle beam irradiation chamber, wherein a first line segment which connects the center of the first opening part and the center of the second opening part does not intersect two side walls constituting the passage, and when a vector which starts from the isocenter to the center of the first opening part is designated as a first vector and a vector which starts from the center of the first opening part to the center of the second opening part is designated as a second vector, a component of the first vector which is parallel to a line segment which connects both ends of the first opening part and a component of the second vector which is parallel to a line segment which connects both ends of the first opening are in an opposite direction.

Advantage of the Invention

According to this invention, it is configured such that a first line segment which connects the center of a first opening and the center of a second opening does not intersect two side walls constituting a passage, and when a vector which starts from an isocenter to the center of the first opening part is designated as a first vector and a vector which starts from the center of the first opening to the center of the second opening part is designated as a second vector, it is configured such that a component, which is parallel to a line segment which connects both ends of the first opening part of the first vector, and a component, which is parallel to a line segment which connects both ends of the first opening part of the second vector are in an opposite direction. That is, according to this invention, it is configured such that from the first opening part to the second opening part of a passage which is surrounded by a shielding wall is tilted. Therefore, in the second opening part, amount of radiation can be decreased and an occupation area of a particle beam irradiation chamber can be reduced. Further, a distance between opening parts of a passage is short. Therefore, a traffic line of a patient or medical personnel from outside an irradiation room to the vicinity of the isocenter is short and the time of bending is small. Consequently, throughput of treatment can be improved.

EMBODIMENTS FOR CARRYING OUT THE INVENTION

Embodiment 1

Figure 1:
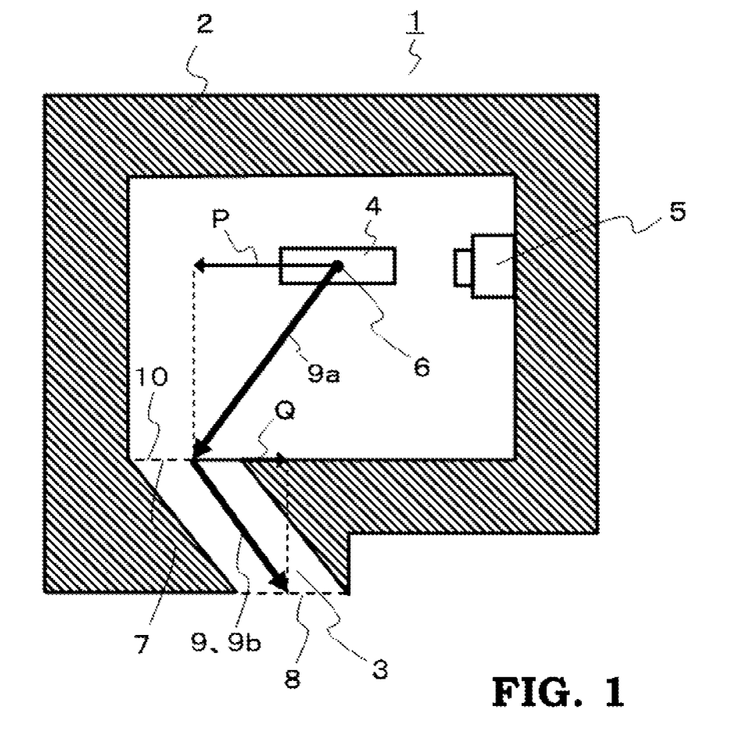
FIG. 1 is a top view showing a particle beam irradiation chamber in Embodiment 1 of this invention.

FIG. 1 is a top view showing a particle beam irradiation chamber in Embodiment 1 of this invention. Four sides of a particle beam irradiation chamber 1 in Embodiment 1 are surrounded by a shielding wall 2, and at one part of the shielding wall 2, a passage 3 is provided. In the particle beam irradiation chamber 1, a treatment table 4 is arranged. Further, a particle beam irradiation nozzle 5 for irradiating a particle beam to a patient who is laid down on the treatment table 4 is provided. A particle beam which is accelerated by an accelerator such as a synchrotron (not shown in FIG.) is transported by a beam transport system to the particle beam irradiation nozzle 5. A target of a particle beam which is irradiated from the particle beam irradiation nozzle 5 is determined on an affected part of the patient who is laid down on the treatment table 4, and a position of the target is called an isocenter 6. The isocenter means the irradiation center which is an intersection point of a particle beam or radiation when a particle beam or radiation is irradiated to a target site (an affected part) from different angles, and the isocenter conforms to the rotation center of the particle beam irradiation nozzle 5. That is, the isocenter is a position where a neutron beam or a photon beam is generated in a particle beam therapy. Further, in Embodiment 1, the particle beam irradiation nozzle 5 is not rotated around the isocenter 6 but is fixed. A particle beam which is transported to an irradiation chamber is formed to be a shape of an affected part, and the particle beam is irradiated by the particle beam irradiation nozzle 5 to the isocenter 6.

A particle beam is irradiated to an affected part of a patient which is in the vicinity of the isocenter 6, therefore, a neutron beam or a photon beam which is generated secondarily is generated from the vicinity of the isocenter 6. Therefore, when neutron shielding design in a particle beam irradiation chamber is performed, in many cases, the isocenter 6 is considered as a radiation source. Radiation which is generated from the vicinity of the isocenter 6 includes not only a neutron beam but also a photon beam, and the limit of total of effective dose of the above-mentioned radiation is determined by law.

A limit value set by law of effective dose of radiation in a particle beam irradiation chamber is different from that of outside a particle beam irradiation chamber. In order to reduce the effective dose outside a particle beam irradiation chamber, design of the passage 3 is important. It is necessary to attenuate the effective dose in a gateway outside the passage 3 so as to be lower than a limit value of the effective dose of radiation outside a particle beam irradiation chamber. In general particle beam therapy, it is known such that regarding the effective dose of radiation, a neutron dose is dominant, therefore, it is important to attenuate a neutron dose to be lower than a limit value set by law in shielding design of a particle beam irradiation chamber. Hereinafter, description of Embodiments of this invention will be made primarily based on shielding of a neutron.

Next, the configuration of the passage 3 in Embodiment 1 will be described referring FIG. 1. Among two gateways of the passage 3, a gateway at the side of the inner wall of the shielding wall 2 is designated as a first opening part 7, and a gateway at the side of the outer wall of the shielding wall 2 is designated as a second opening part 8. In this time, it is configured such that a first line segment 9 which connects the center of the first opening part 7 and the center of the second opening part 8 does not intersect both walls of the passage 3. Further, when a vector which starts from the isocenter 6 to the center of the first opening part 7 is designated as a first vector 9a, a vector which starts from the center of the first opening part 7 to the center of the second opening part 8 is designated as a second vector 9b and a line segment which connects both ends of the first opening part 7 is designated as a line segment 10, it is configured such that both of a component P of the first vector 9a in a line segment direction 10 and a component Q of the second vector 9b in a line segment direction 10 are non-zero and the component P and the component Q are in the opposite direction. Further, in other words, in a case where a line segment which connects the isocenter and the center of the first opening part is designated as a first line segment and a line segment which connects the center of the first opening part and the center of the second opening part is designated as a second line segment, it is configured such that the first line segment and the second line segment are formed to be a shape of symbol of a sign of inequality, "<" or ">".

In the passage 3 having the above-mentioned configuration, a gateway inside the particle beam irradiation chamber 1 (the first opening part) can be seen from a gateway outside the particle beam irradiation chamber 1 (the second opening part). Further, in a case where a width of the first opening part and that of the second opening part are same, a width of the passage 3 is narrower than that of the first opening part and that of the second opening part. In other words, in a case where the shielding wall 2 of the particle beam irradiation chamber 1 is formed to be a rectangle as shown in FIG. 1, the passage 3 has an oblique shape.

Figure 2:
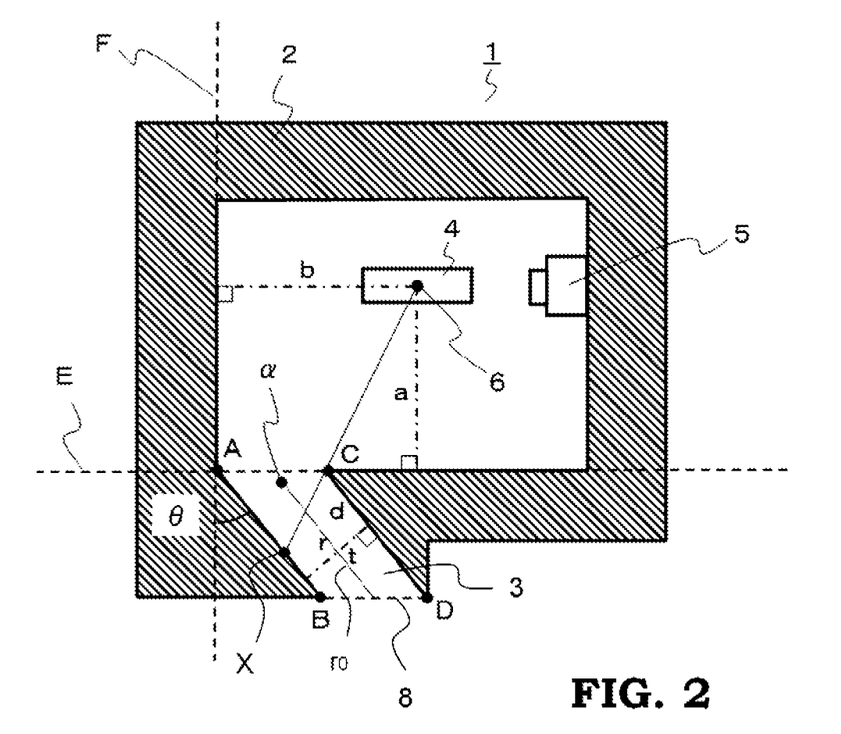
FIG. 2 is a view for describing a shielding effect of a particle beam irradiation chamber in Embodiment 1 of this invention.

FIG. 2 is a view for describing a shielding effect in a particle beam irradiation chamber in Embodiment 1 of this invention. In FIGS. 2, A and C are points of both ends of a gateway inside the particle beam irradiation chamber 1, and B and D are points of both ends of a gateway outside the particle beam irradiation chamber 1. A length of a perpendicular line which starts from the isocenter 6 to a straight line E which connects both ends of a gateway inside the particle beam irradiation chamber 1 is designated as a. A length of a perpendicular line which starts from the isocenter to a straight line F which is perpendicular to the straight line E, which connects both ends of a gateway inside the particle beam irradiation chamber 1, and passes a point which is farther away from the isocenter 6 among points of both ends of a gateway inside the particle beam irradiation chamber 1, (in a case of FIG. 2, a point of A) is designated as b. It is assumed such that inner walls of both sides of the passage part are parallel planes, and a distance between the wall surfaces is designated as t. Further, an angle which is formed by the straight line F which is perpendicular to the straight line E which connects both ends of a gateway inside the particle beam irradiation chamber 1 and an inner wall of a passage part is designated as θ.

It is known such that as shown in the Literature "shielding calculation practical manual 2007 2-13 to 2-14", a neutron dose obeys following formula (1) and (2) of Nakamura-Uemino.

In order to use the formulas of Nakamura-Uemino, it is necessary to set a virtual source at a gateway inside a particle beam irradiation chamber (a first opening part). A position of a virtual source is a point where the square attenuation of the distance in the passage 3 starts, and the point is set to be point α, that is, a point which is shifted to the side of inside of a particle beam irradiation chamber by the half of a passage from the center of gravity of a surface of a passage width in a line segment which connects the isocenter and a point X which is a critical point where radiation can be reached directly in the passage. Dose $H_0$ in the virtual source α is obtained by the following formula (1). Here, $D_0$ is a standardization constant (dose in the distance from a source of 1 m), R is a distance from a radiation source (isocenter) to a virtual radiation source α, s is a value which is obtained by dividing the geometric mean of a breadth and a depth of an irradiation chamber by 2, S is the total surface area of an inner surface of a particle beam irradiation chamber and S' is the surface area of an inner surface of a particle beam irradiation chamber which can be looked directly from a virtual radiation source position.

$$H_0 = D_0 \left( \frac{1}{R^2} + \frac{4}{R^2 + 4s^2 - 2\sqrt{2} Rs} \frac{S'}{S} \right) \quad (1)$$

Further, dose $I(r)$ of radiation in a passage is obtained by a numerical formula (2). Here, r is a distance from a virtual radiation source α.

$$I(r) = H_0 \frac{(t/2)^2}{r^2} \quad (2)$$

As can be seen from formula (2), dose in a passage is attenuated by a reciprocal number of square of a distance, therefore, when a distance between X and B is longer, dose in a second opening part (a gateway outside a particle irradiation chamber) can be reduced. Dose $H_0$ at a position of a virtual radiation source α is smaller when a distance from an isocenter (radiation source) to a virtual radiation source α is longer. However, as can be seen such that the second member is in parentheses of formula (1), attenuation of whole of $H_0$ is smaller than square of a distance. The second member is a member for showing an influence of scattering in a particle beam irradiation chamber. Therefore, in a case where whole distance of a route from outside an irradiation chamber to an isocenter 6 in a chamber is fixed, accordingly, dose in the vicinity of a gateway outside a particle beam irradiation chamber can be reduced not by keeping a position of a virtual radiation source α away from a radiation source but by making a distance $r_0$ from a virtual radiation source α to a second opening part 8 longer. In other words, whether dose can be suppressed to be in a range of a isocenter or not is practically determined by a length of $r_0$. Consequently, under the condition such that $r_0$ is fixed, a length of a route of a passage is shorter when a passage is formed to have an oblique shape as shown in Embodiment 1.

A distance $r_0$ from a virtual radiation source α to a second opening part 8 can be obtained by calculating using following formula (3), a, b, d, t and θ which are parameters showing the configuration of a particle beam irradiation chamber.

$$d = \frac{at}{2(a\sin\theta + b\cos\theta - t)\cos\theta} + r_0 - \frac{t}{2} \qquad (3)$$

Figure 3:
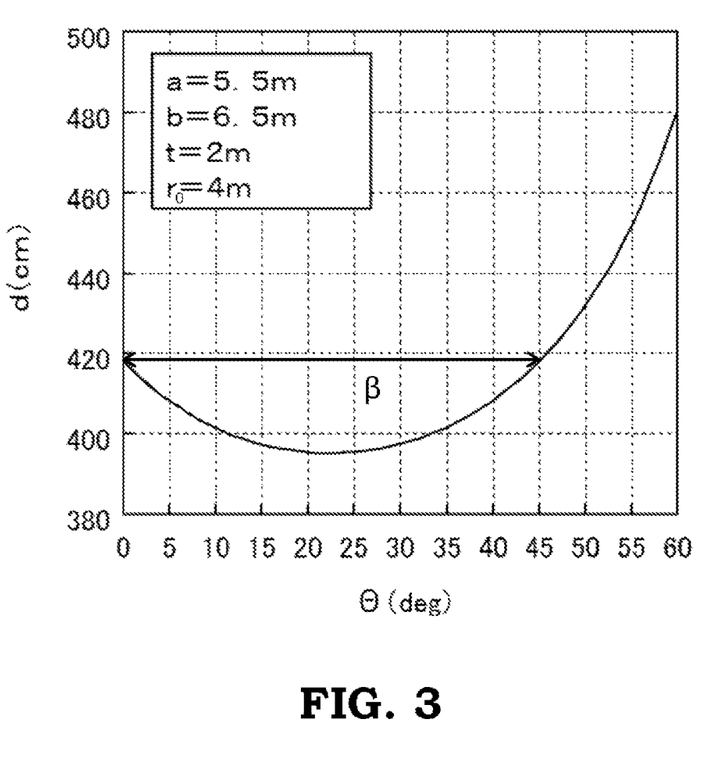
FIG. 3 is a graph showing a size of a passage of a particle beam irradiation chamber in Example 1 of this invention.

FIG. 3 shows a length d of the passage which is obtained by calculating with formula (3) using θ as a parameter. For example, a=5.5 m, b=6.5 m, t=2.5 m, $r_0$=4 m. As can be seen from formula (3), when θ satisfies following formula (4), a value of d is smaller in comparison with a case of θ=0°.

$$(a \sin \theta + b \cos \theta - t)\cos \theta > b - t \qquad (4)$$

Therefore, θ is a value which satisfies 0°<θ<90° and formula (4) (a range of β in FIG. 3), in comparison with a case of θ=0°, the same level of shielding effect can be obtained with a shorter length of d. Further, θ>0° means such that a straight line E which connects both ends of a gateway inside a particle beam irradiation chamber does not intersect wall surfaces of both sides of a passage by an angle which is not perpendicular, and a passage having the above-mentioned is expressed as an oblique passage in Embodiment 1.

By arranging an oblique passage 3 as above-mentioned, in a case where dose outside an irradiation chamber is suppressed to be lower than a certain value, under the condition in which a distance $r_0$ for attenuating in a passage is fixed, a length of a passage d can be shortened, as a result, an occupation area can be reduced. Further, as a passage is not bending, a traffic line of a patient which is from an entrance of a particle beam irradiation room to a treatment bed and a traffic line of medical personnel are not complicated. Consequently, the time which is required before starting treatment or the time which is required for a patient to leave a chamber after treatment can be shortened, as a result, throughput of treatment can be improved.

Embodiment 2

Figure 4:
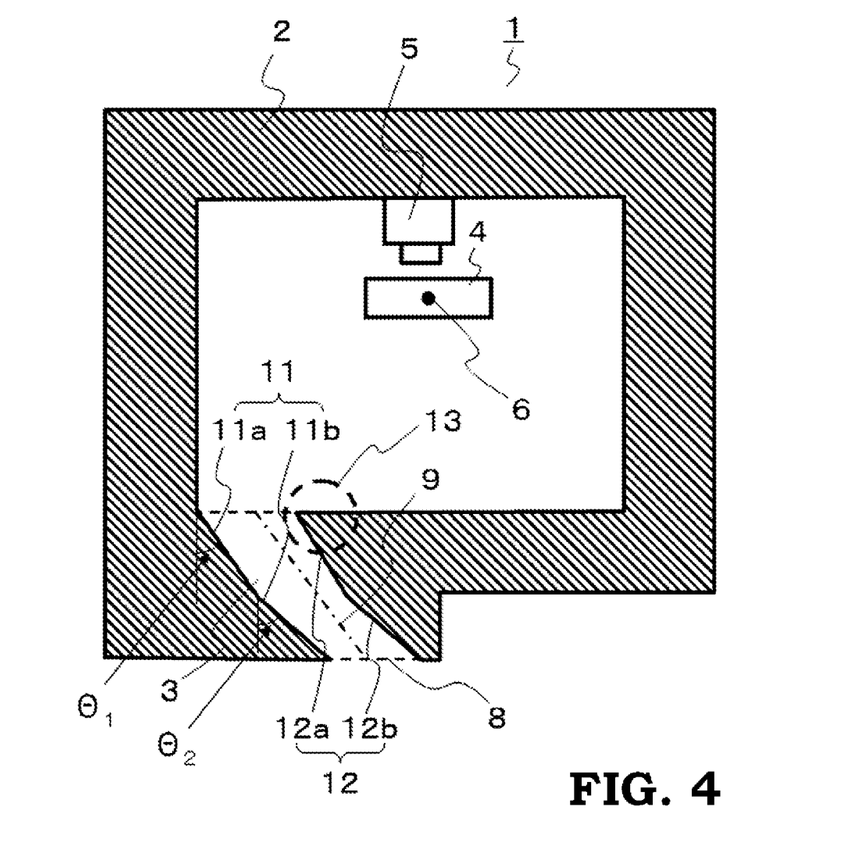
FIG. 4 is a top view showing a particle beam irradiation chamber in Embodiment 2 of this invention.

FIG. 4 is a top view showing a particle beam irradiation chamber in Embodiment 2 of this invention. The configuration of a particle beam irradiation chamber 1 in Embodiment 2 is same as that of a particle beam irradiation chamber 1 in Embodiment 1. However, unlike Embodiment 1, side walls of both sides constituting a passage 3 are configured by a combination of two plane surfaces, respectively. In addition to that, a position of a particle beam irradiation nozzle 5 is different. In Embodiment 2, the particle beam irradiation nozzle 5 is provided at a surface opposing a surface of a shielding wall where the passage 3 is provided.

It is known such that regarding a neutron beam which is generated by an interaction of a particle beam and a target, the strength of high-energy neutron beam which is generated per a solid angle is stronger at a direction which is nearer to a travelling direction of an original incident particle beam. As the energy of a neutron beam is higher, the probability of passing through a shielding wall is higher. Consequently, at a position of a particle beam irradiation nozzle in Embodiment 2 (a direction of an incident beam), the strength of a neutron beam which reaches a shielding wall at a side of a passage (a number of a neutron) and the energy is larger than that at a position of a particle beam irradiation nozzle in Embodiment 1. Therefore, it is preferable such that a thickness of a part 13 of a shielding wall which shields a neutron beam which directly reaches a passage and a gateway outside a particle beam irradiation chamber is secured.

Regarding a particle beam irradiation chamber in Embodiment 2, as shown in FIG. 4, one side of a side wall 11 of the passage 3 is constituted by a plane surface 11a and a plane surface 11b, and another side of a side wall 12 of the passage 3 is constituted by a plane surface 12a and a plane surface 12b. However, in the same as that of Embodiment 1, it is configured such that a first line segment 9 which connects the center of a first opening part 7 and the center of a second opening part 8 does not intersect both sides of side walls of the passage 3. That is, the passage 3 is gently bended on the way. When an angle which is formed by the plane surface 11a and a direction in a thickness of a shielding wall is designated as θ1, and an angle which is formed by the plane surface 11b and a direction in a thickness of a shielding wall is designated as θ2, by making the condition to be θ1<θ2, a thickness of the part 13 of a shielding wall can be thicker.

By constituting a particle beam irradiation chamber as above-mentioned, in the same way as that of Embodiment 1, an occupation area can be reduced. Further, a length of a passage is shorter and the passage is not bended greatly. Therefore, a traffic line of a patient which is from an entrance of a particle beam irradiation room to a treatment bed and a traffic line of medical personnel are not complicated. Consequently, the time which is required before starting treatment or the time which is required for a patient to leave a chamber after treatment can be shortened, as a result, throughput of treatment can be improved. Further, in Embodiment 2, both sides of side walls constituting a passage are constituted by a combination of two plane surfaces. Therefore, in comparison with a thickness of a particle beam irradiation chamber in Embodiment 1, a thickness of the shielding wall 2 of the part 13 of a shielding wall in the vicinity of the first opening part 7 can be made thicker. As a result, radiation which passes through the part of a shielding wall 13 to be incident on the passage 3 can be further attenuated.

Embodiment 3

Figure 5:
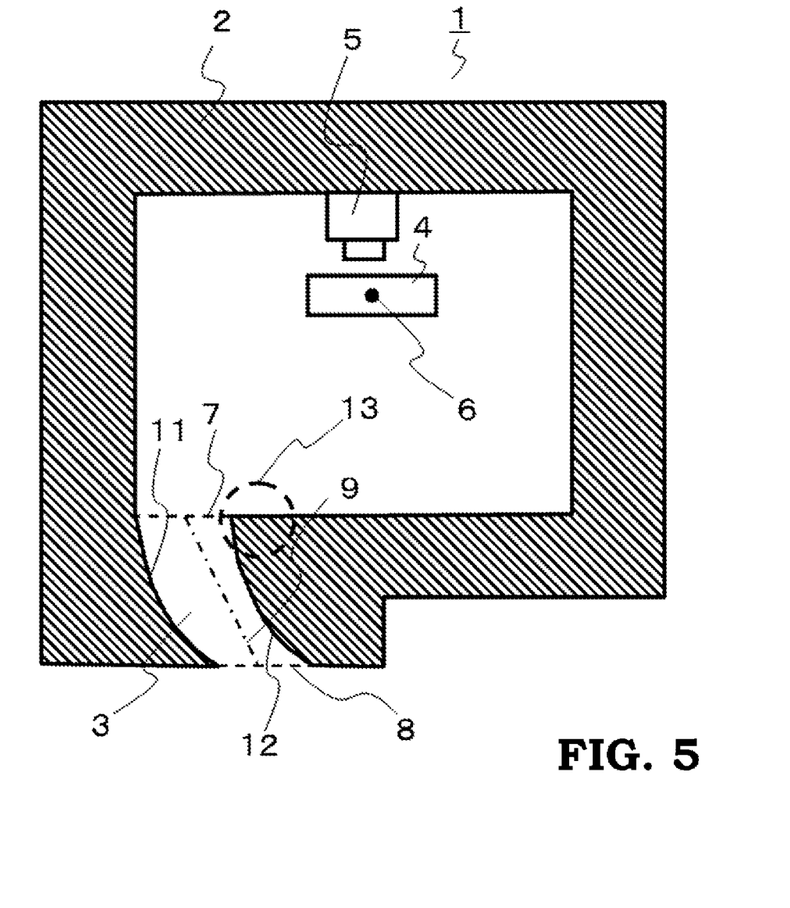
FIG. 5 is a top view showing a particle beam irradiation chamber in Embodiment 3 of this invention.

FIG. 5 is a top view showing a particle beam irradiation chamber in Embodiment 3 of this invention. The configuration of a particle beam irradiation chamber 1 in Embodiment 3 is same as that of a particle beam irradiation chamber 1 in Embodiment 2, however, unlike Embodiment 2, configured such that side walls of both sides constituting a passage 3 are configured by a curved surface.

As shown in FIG. 5, regarding a particle beam irradiation chamber in Embodiment 3, both sides of side walls of the passage 3 are constituted by a gentle curved surface. However, in the same way as that in Embodiment 1, it is configured such that a first line segment 9 which connects the center of a first opening part 7 and the center of a second opening part 8 passes the inside of the passage 3. That is, by making the passage 3 to be a gentle curved line, a thickness of a part 13 of a shielding wall can be thicker.

As constituting a particle beam irradiation chamber as the above-mentioned, in the same way as that of Embodiment 1, an occupation area of a particle beam irradiation chamber can be reduced. Further, a length of a passage is shorter and the passage is not bended greatly. Therefore, a traffic line of a patient which is from an entrance of a particle beam irradiation room to a treatment bed and a traffic line of medical personnel are not complicated. Consequently, the time which is required before starting treatment or the time which is required for a patient to leave a chamber after treatment can be shortened, as a result, throughput of treatment can be improved. Further, in Embodiment 2, both sides of side walls constituting a passage are constituted by a curved surface.

Therefore, in comparison with a thickness of a particle beam irradiation chamber in Embodiment 1, a thickness of a part 13 of a shielding wall 2 in the vicinity of a first opening part 7 can be made thicker. As a result, radiation which passes through to be incident on the passage 3 can be further attenuated.

Embodiment 4

Figure 6:
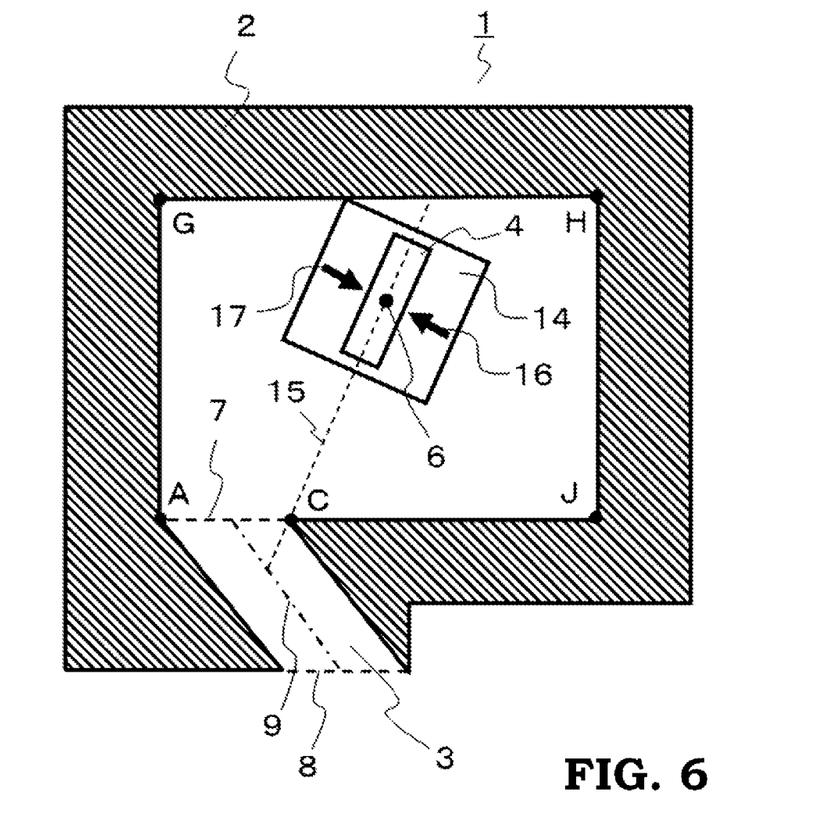
FIG. 6 is a top view showing a particle beam irradiation chamber in Embodiment 4 of this invention.

FIG. 6 is a top view showing a particle beam irradiation chamber in Embodiment 4 of this invention. The configuration of a particle beam irradiation chamber 1 in Embodiment 4 is same as that of a particle beam irradiation chamber 1 in Embodiment 1, however, unlike Embodiment 1, it is configured such that a rotary gantry device 14 is provided instead of a particle beam irradiation nozzle. Further, as shown in FIG. 6, four corners of an inner surface of a shielding wall 2 are designated as A, G, H and J.

A rotary gantry device comprises a particle beam irradiation nozzle and a group of electromagnets for transporting a particle beam, the particle beam irradiation nozzle can be rotated by approximately 360 degrees, in the rotation center, a hollow space is provided, and in the hollow space, a treatment bed 4 is arranged. Regarding the rotary gantry device 14, treatment can be performed by rotating a particle beam irradiation nozzle around the treatment table 4 so as to irradiate a particle beam from a desired angle. Consequently, an isocenter 6 in Embodiment 4 is the rotation center (irradiation center) of the rotary gantry device 14. FIG. 6 shows a section including the isocenter 6, and an axis of rotation of the rotary gantry device 14 is designated as a straight line 15.

In Embodiment 4, as shown in FIG. 6, it is configured such that the first opening part 7 is not on a plane surface which passes through the isocenter and is perpendicular to the axis of rotation of the rotary gantry device 14. It is further preferable such that an intersection point of the straight line 15 which is parallel to an axis of rotation of the rotary gantry device 14 and is extended from the isocenter 6 to a side of a passage, and a first line segment 9 which connects the center of a first opening part 7 and the center of a second opening part 8 is in a passage 3. It is simply that an arrangement direction of the rotary gantry 14 is determined.

A neutron beam which is generated from a target (isocenter) is influenced by momentum of an incident particle beam. For example, in a case where a particle beam is irradiated to a target from right above, the strength of the high-energy neutron beam in a direction of right under (in a direction toward a floor) is high. On the contrary, in a case where a particle beam is irradiated to a target from right under, the high-energy having high strength in a direction of a ceiling is generated. From the point of view of a neutron dose in a passage, by preventing the high-energy neutron beam which is generated from an isocenter to a direction of an angle which is approximately parallel to an incident direction of a particle beam from reaching directly a passage, especially a first opening part 7, the dose at an outside of the second opening part 8 can be decreased.

As described in Embodiment 4, by arranging a rotary gantry device, in a case where a particle beam is irradiated from a direction which is parallel to a floor face, designated by arrow 16, the—high energy neutron beam which is generated from an isocenter is emitted to a direction which includes a side wall between AG of a shielding wall 2. On the other hand, in a case where a particle beam is irradiated from a direction which is parallel to a floor face, designated by arrow 17, the—high energy neutron beam which is generated from an isocenter is emitted to a direction which includes a side wall between HJ of the shielding wall 2.

As above-mentioned, by specifying the positional relationship of the a rotary gantry device and a passage, the strength of a direct neutron beam which is emitted to a direction of a first opening part 7 becomes smaller relatively, as a result, in comparison with a case in which the positional relationship between a rotary gantry device and a passage is not considered, a neutron dose in a second opening part 8 can be reduced.

Embodiment 5

Figure 7:
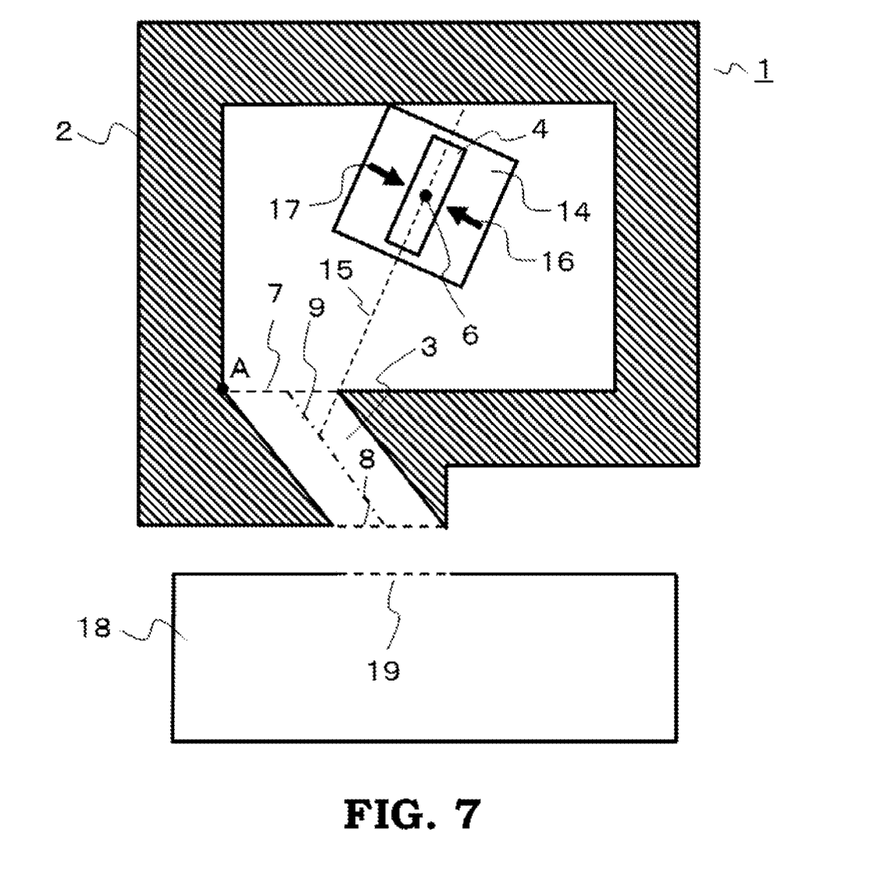
FIG. 7 is a top view showing a particle beam irradiation chamber in Embodiment 5 of this invention.

FIG. 7 is a top view showing a particle beam irradiation chamber in Embodiment 5 of this invention. The configuration of a particle beam irradiation chamber 1 in Embodiment 5 is same as that of a particle beam irradiation chamber 1 in Embodiment 4. In Embodiment 5, a positioning chamber 18 is arranged in front of a particle beam irradiation chamber 1.

In Embodiment 5, in front of a gateway outside a particle beam irradiation chamber (second opening part) 8, a gateway 19 of the positioning chamber 18 is arranged adjoiningly. A positioning chamber is a chamber where the relative relationship between a perspective image of a body of a person to be treated (patient) and a treatment table is photographed in advance by an x-ray imaging device, for example. In advance, the relative relationship between a body of a patient and a treatment table is photographed in the positioning chamber 18, just before a particle beam therapy, a patient who is laid on a treatment table is carried in a particle beam irradiation chamber 1, and the treatment table is set at a position of an isocenter 6. The relationship between the treatment table 4 which is fixed on a position of the isocenter 6 and the isocenter 6 is determined in advance. Accordingly, by doing the above-mentioned, it is not necessary to adjust a position of an isocenter and that of a patient in the particle beam irradiation chamber 1, or even in a case where it is necessary to adjust a position of an isocenter and that of a patient, only fine adjustment is required. Consequently, the time which is required for adjustment is shorter in comparison with conventional particle beam irradiation chambers.

In this time, it is necessary to carry a patient who is laid on a treatment table to a predetermined position in a particle beam irradiation chamber 1 after a perspective image of a body of a patient is photographed in advance by using an x-ray imaging device. In some cases, the relationship between a body of a patient and a treatment table may be changed by movement of a patient. In a conventional case in which a passage is bended, it is necessary to change a direction of a treatment table many times, and in a case in which a moving distance is long, the probability of changing the relative positional relationship between a body of a patient and a treatment may be higher.

As described in Embodiment 5, by forming a passage 3 in a particle beam irradiation chamber 1 to be a linear passage, a traffic line can be shortened. In addition to that, a treatment table can be moved linearly. Consequently, it is only necessary to change a direction of a treatment table once while moving to an isocenter. As a result, the probability of changing the relative positional relationship between a body of a patient and a treatment table can be reduced.

In a conventional particle beam therapy, an x-ray imaging device is provided in a particle beam irradiation chamber and an x-ray penetrative photographing for positioning is performed while a patient is laid on a treatment table in an isocenter. After that, particle beam therapy is performed. However, as an x-ray penetrative photographing for positioning and a particle beam therapy are performed in the same particle beam irradiation chamber, there is a problem such that an occupation time in a particle beam irradiation chamber per one therapy is long.

As described in Embodiment 5, when an x-ray penetrative photographing for positioning is performed in a positioning chamber in advance, and only a particle beam therapy is performed in a particle beam irradiation chamber, improvement of throughput of treatment can be expected. Especially, in a small facility having only one particle beam irradiation chamber, during therapy of one patient in a particle beam irradiation chamber, positioning of subsequent patient can be performed in a positioning chamber, therefore therapy can be performed more effectively.

REMARKS 1. particle beam irradiation chamber
2. shielding wall
3. passage
4. treatment table
5. particle beam irradiation nozzle
6. isocenter
7. first opening part
8. second opening part
9. first line segment
9a. first vector
9b. second vector
10. line segment
11, 12. side wall
13. a part of a shielding wall
14. rotary gantry device
15. straight line
16, 17. arrow
18. positioning chamber
19. gateway

The invention claimed is:

1. A particle beam irradiation chamber in which a passage having a first opening part at the side of an inner wall and a second opening part at the side of an outer wall is provided, an isocenter is provided inside the particle beam irradiation chamber,
    wherein a first line segment which connects the center of the first opening part and the center of the second opening part does not intersect two side walls constituting the passage, when a vector which starts from the isocenter to the center of the first opening part is designated as a first vector and a vector which starts from the center of the first opening part to the center of the second opening part is designated as a second vector, a component of the first vector which is parallel to a line segment which connects both ends of the first opening part and a component of the second vector which is parallel to a line segment which connects both ends of the first opening are in an opposite direction, and
    $\theta$ is an angle larger than 0 degree and smaller than 90 degrees and is an angle which satisfies $(a*\sin\theta + b*\cos\theta - t)\cos\theta > b - t$,
    where a is a length of a perpendicular line which starts from the isocenter to a straight line E which connects both ends of the first opening part, b is a length of a perpendicular line which starts from the isocenter to a straight line F which is perpendicular to the straight line E, and passes a point which is farther away from the isocenter among points of both ends of the first opening part, t is a width of the passage, and $\theta$ is an angle which is formed by the straight line F and inner wall of the passage.

2. The particle beam irradiation chamber according to claim 1,
    wherein among two side walls constituting the passage, at least one side wall, from the first opening part to the second opening part, is constituted by a plurality of surfaces.

3. The particle beam irradiation chamber according to claim 1,
    wherein among two side walls constituting the passage, at least one side wall, from the first opening part to the second opening part, is constituted by a curved surface.

4. The particle beam irradiation chamber according to claim 1,
    wherein the isocenter is the rotation center of a rotary gantry device with which a particle beam irradiation nozzle is equipped, and the first opening part is not on a plane surface which passes the isocenter and is perpendicular to an axis of rotation of the rotary gantry device.

5. The particle beam irradiation chamber according to claim 1,
    wherein the isocenter is the rotation center of a rotary gantry device with which a particle beam irradiation nozzle is equipped, and a straight line, which is parallel to an axis of rotation of the rotary gantry device and starts from the isocenter and is extended to a passage side, intersects the first line segment in the passage.

6. The particle beam irradiation chamber according to claim 1,
    wherein a gateway of a positioning chamber is arranged in a position opposing the second opening part.

7. The particle beam irradiation chamber according to claim 1,
    wherein $\theta$ is an angle between 15 degrees and 30 degrees.

* * * * *